United States Patent [19]

Tsuji et al.

[11] Patent Number: 5,494,877
[45] Date of Patent: Feb. 27, 1996

[54] CHROMIUM-BASED FLUORINATION CATALYST CONTAINING GALLIUM AND PRODUCTION METHOD THEREOF

[75] Inventors: Katsuyuki Tsuji; Tetsuo Nakajo, both of Kanagawa, Japan

[73] Assignee: Showa Denko K. K., Tokyo, Japan

[21] Appl. No.: 352,821

[22] Filed: Dec. 1, 1994

Related U.S. Application Data

[63] Continuation-in-part of Ser. No. 262,496, Jun. 20, 1994, and a continuation-in-part of Ser. No. 301,881, Sep. 7, 1994.

[51] Int. Cl.6 .................. B01J 27/132; B01J 27/125; B01J 37/26
[52] U.S. Cl. .................. 502/228; 502/104; 502/231
[58] Field of Search .................. 502/104, 120, 502/224, 228, 231, 242; 570/166, 168

[56] References Cited

U.S. PATENT DOCUMENTS 3,859,424  1/1975  Scherer et al. .................. 423/472

FOREIGN PATENT DOCUMENTS

| | | |
|---|---|---|
| 2084864 | 12/1992 | Canada . |
| 0502605 | 9/1992 | European Pat. Off. . |
| 0629440 | 12/1994 | European Pat. Off. . |
| 0641598 | 3/1995 | European Pat. Off. . |
| 55-27139 | 2/1980 | Japan . |
| 55-27138 | 2/1980 | Japan . |
| 5269382 | 10/1993 | Japan . |
| 955083 | 4/1964 | United Kingdom .................. 570/166 |
| 1113658 | 5/1968 | United Kingdom .................. 570/166 |

*Primary Examiner*—Shrive Beck
*Assistant Examiner*—Fred J. Parker
*Attorney, Agent, or Firm*—Sughrue, Mion, Zinn, Macpeak & Seas

[57] ABSTRACT

To produce hydrofluorocarbons with high productivity, and to provide a catalyst for that purpose and a production method of the catalyst, there is provided a chromium-based fluorination catalyst comprising Cr, Ga, O and F as the essential constituent elements, wherein a Ga/Cr atomic ratio is from 0.001 to 0.15. The catalyst is prepared by particularly fluorinating a precursor of an oxide or a hydroxide. HF and a halogenated hydrocarbon are brought into contact in a gaseous phase in the presence of this catalyst.

9 Claims, No Drawings

CHROMIUM-BASED FLUORINATION CATALYST CONTAINING GALLIUM AND PRODUCTION METHOD THEREOF

This is a Continuation-in-Part of application Ser. Nos. 08/262,496 filed Jun. 20, 1994 and 08/301,881 filed Sep. 7, 1994.

BACKGROUND OF THE INVENTION

1. Field of the Invention

When producing those hydrofluorcarbons which do not contain chlorine and are hence free from destruction of the ozone layer (hereinafter referred to as "HFC"), among others, difluoromethane (hereinafter referred to as "HFC-32"), 1,1,1,2-tetrafluoroethane (hereinafter referred to as "HFC-134a") and pentafluoroethane (hereinafter referred to as "HFC-125"), the present invention relates to a fluorination catalyst improved for producing the HFCs with high productivity, a production method of the fluorination catalyst, and a method of efficiently producing the HFCs by bringing hydrogen fluoride and a halogenated hydrocarbon into mutual contact in a gaseous phase by using the catalyst.

2. Description of the Related Art

A typical example of the industrial production methods of the HFCs is the method which replaces halogens other than F by F by bringing a hydrogen-containing halogenated hydrocarbon into contact with HF (in many cases, addition of HF using an unsaturated halogenated hydrocarbon as the starting material and the exchange reaction of the halogens other than F with F are simultaneously conducted). However, the reaction does not smoothly proceed in most cases, and the production quantity of the HFCs greatly depends on the catalyst used.

An example of the most difficult reaction is the synthesizing reaction of HFC-134a by fluorination of 1-chloro-2,2,2-trifluoroethane (hereinafter referred to as "HCFC-133a"), and this reaction is an endothermic reaction which is not advantageous thermodynamically. Therefore, the reaction is generally carried out at a relatively high temperature by allowing HF in an amount exceeding a stoichiometric amount to be co-present with HCFC-133a. According to Japanese Unexamined Patent Publication (Kokai) No. 55-27138, for example, HFC-134a is obtained at a yield of 32% by conducting the reaction at a temperature of 400° C. using a compound obtained by treating $CrF_3 \cdot 3H_2O$ with air, as the catalyst. The reaction at such a high reaction temperature promotes coking of the catalyst and reduces catalyst life. To prevent coking, an attempt was made to allow oxygen to be co-present inside the reaction gas (Japanese Unexamined Patent Publication (Kokai) No. 55-27139), but this method is not desirable because chlorinated by-products increase. To restrict the formation of the chlorinated by-products, Japanese Examined Patent Publication (Kokoku) No. 5-88690 discloses a method which conducts the reaction in the presence of oxygen by using the catalyst which is obtained by fluorinating a non-Cr-based $CoCl_2/Al_2O_3$, but this catalyst has low activity and low productivity. For these reasons, examinations have so far been made so as to prolong service life of the catalysts. In other words, Japanese Unexamined Patent Publication (Kokai) No. 2-172933 clarifies that a catalyst comprising a halide or oxide containing at least one kind of elements selected from the group consisting of Al, Mg, Ca, Ba, Sr, Fe, Ni, Co and Mn, and containing also Cr, has high durability (long life). EP 502605 discloses a Cr-based catalyst supporting Zn. Further, Japanese Unexamined Patent Publication (Kokai) No. 4-34694 discloses a catalyst comprising $Cr_2O_3$ which is partially fluorinated and supports Ru and Pt, and Japanese Unexamined Patent Publication (Kokai) No. 5-269382 discloses a catalyst consisting of chromium oxide and nickel oxide as principal components thereof, as a catalyst having long service life.

However, coking of the catalyst is vigorous in the fluorination reaction of the hydrogen-containing halogenated hydrocarbon as the production method of the HFCs, and even the catalysts described above do not have sufficient life. In other words, it has been necessary in the past to select the reaction condition under which coking difficultly occurs. Because the progress of coking is greater when the ratio of the HF feed quantity to the feed quantity of organic materials (hereinafter called the "molar ratio") is smaller, the progress of coking is retarded by increasing this molar ratio when the conventional fluorination catalyst is used. However, the increase of the molar ratio means the decrease of the feed quantity of the organic materials (when SV is kept constant), and means the drop of STY (space time yield). It can be therefore concluded that catalyst life is prolonged according to the prior art at the sacrifice of STY to a certain extent.

Accordingly, if a catalyst which makes coking more difficult than the conventional catalysts and which has longer service life could be obtained, it becomes possible not only to prolong catalyst life but also to carry out the reaction at a lower molar ratio, so that the improvement of productivity can be also expected.

In the light of the background described above, the present invention aims at providing a fluorination catalyst having long service life in the production of the HFCs, and a method of efficiently producing the HFCs by bringing a halogenated hydrocarbon having 1 to 4 carbon atoms into contact with HF in a gaseous phase by using the catalyst described above.

SUMMARY OF THE INVENTION

The inventors of the present invention have earnestly carried out their studies so as to solve the problems described above, and have found out that a catalyst containing Ga, Cr, O and F as the essential constituent elements wherein the atomic ratio of Ga to Cr is within a range of 0.0001 to 0.15, preferably 0.001 to 0.1 and particularly preferably 0.003 to 0.05, has remarkably longer life than the conventional Cr-based fluorination catalysts. The present invention has thus been completed.

Accordingly, the present invention provides:

(1) a catalyst containing Ga, Cr, O and F as the essential catalyst constituent elements, wherein the atomic ratio of Ga to Cr is within a range of 0.0001 to 0.15, preferably 0.001 to 0.1 and particularly preferably 0.003 to 0.05;

(2) a production method of the catalyst (1) which comprises bringing a catalyst precursor containing a Cr element and a Ga element into contact with fluorine, hydrogen fluoride or fluorine-containing hydrocarbon and conducting fluorination treatment; and (3) a method of fluorinating a halogenated hydrocarbon which comprises bringing a halogenated hydrocarbon into contact with HF in the presence of the catalyst (1).

DESCRIPTION OF PREFERRED EMBODIMENTS

Although it is not much preferred that the chromium-based fluorination catalyst according to the present invention contains large quantities (in the wt % order) of alkali metals as constituent elements other than Ga, Cr, O and F, the catalyst may contain other elements in the % order. Particularly, at least one kind of elements selected from the Groups 8, 9, 10, 11 and 12 (New IUPAC Naming Method), among others, Co, Ni, Cu, Zn, Cd, etc., which are expected to provide an activity promotion effect as a promoter or a co-catalyst, may be contained within the range of 0.001 to 0.5 and preferably 0.003 to 0.2, in terms of the atomic ratio to Cr.

The catalyst according to the present invention can be prepared by using a compound containing Ga and Cr (e.g. an oxide and a hydroxide) as a catalyst precursor, fluorinating this catalyst precursor by HF, $F_2$ or a halogenated hydrocarbon containing fluorine in the molecules thereof, and so replacing partially O and OH by fluorine. The compounds containing Ga and Cr can be supported on a support, and examples of suitable supports include activated carbon, alumina, aluminum fluoride, magnesium fluoride, and so forth.

Any of known methods such as a kneading method, an impregnation method, a coprecipitation method, etc., can be employed as the method of preparing the catalyst precursor, and any materials can be used for the starting materials for preparing the catalyst precursor so long as they are available on the industrial scale. Among the methods described above, the impregnation method and the coprecipitation method are preferred because they can introduce Ga in Cr in a high dispersion. Among others, coprecipitation is further preferred because this method can arbitrarily control the dispersion state of Ga. Accordingly, an example of the preferred method of preparing the catalyst precursor comprises the steps of allowing a solution dissolving therein the salts of Ga and Cr to react with a precipitating agent to form a precipitate, and conducting filtration, washing, drying and firing of the precipitate (example of the coprecipitation method), or the steps of allowing chromium oxide or chromium hydroxide to be impregnated with a solution of the Ga compound, and conducting drying and firing (example of the impregnation method). When the support is used, the catalyst precursor can be prepared by allowing the support to be impregnated with the solution dissolving the Ga and Cr compounds, and conducting drying and firing.

Examples of further preferred methods of preparing the catalyst precursor includes the method which comprises adding in advance a precipitating agent (an alkali) to a slurry of chromium hydroxide (particularly trivalent hydroxide) in an amount sufficient enough to neutralize at least the Ga and Cr salts to be later added, then adding slowly a mixed solution of the Ga and Cr salts, and conducting separation, washing, drying and firing of the resulting product, and the method which comprises dropping either simultaneously or alternately a solution dissolving the Ga and Cr salts and a precipitating agent so as to form a slurry while controlling the reaction solution so that its pH is from 6 to 12 and particularly preferably, 6.5 to 10, and then conducting filtration, washing, drying and firing of the reaction product.

Nitrates, chlorides and sulfates can be suitably used as the Ga and Cr compounds as the starting materials for the preparation of the catalyst precursor. Among them, the nitrates and the chlorides are particularly preferred for the coprecipitation method and the impregnation method, respectively. Preferred examples of precipitating agents are ammonia, sodium hydroxide, sodium carbonate, sodium/n hydrogencarbonate, potassium hydroxide, potassium carbonate, potassium hydrogencarbonate, ammonium carbonate and ammonium hydrogencarbonate. Particularly preferred among them is ammonia.

When a molded shape is desired as the shape of the catalyst, tablet-molding is carried out before, or after, firing described above, or extrusion molding is carried out before drying.

Drying is preferably carried out at a temperature within the range of 80° to 130° C., particularly 90° to 120° C., in an atmosphere of an air or an inert gas such as $N_2$, for at least 30 minutes, but other drying methods such as vacuum drying can also be made.

Firing is carried out at a temperature within the range of 300° to 600° C., preferably 350° to 500° C., but the firing atmosphere must be selected depending on the preparation method employed. In other words, when a chromium compound such as chromium hydroxide, chromium oxide, etc., comes into contact with $O_2$ at a high temperature of above about 350° C., a drastic drop of the specific surface area occurs, and in the case of activated carbon, it is burnt and extinguished. Accordingly, when the chromium compound is used as the principal component of the catalyst precursor without using the support or when active carbon is used as the support, it must not be exposed to the atmosphere containing $O_2$ at 1,000 Pa (absolute pressure) at a temperature of not lower than 350° C., and firing is preferably carried out in an inert gas, such as $N_2$, Ar, etc., or reducing gas atmosphere. The term "reducing gas atmosphere" hereby used means the atmosphere containing a gas having reducing power such as $H_2$, CO, NO, etc., and may include other inert gases and moisture. An oxidizing gas such as $O_2$ may be contained in a concentration which does not render any safety problem, but is not contained preferably.

When alumina or various metal fluorides are used as the support, firing can be carried out in the $O_2$-containing atmosphere, typically in air, because the support provides the effect of preventing the drop of the specific surface area even in the $O_2$ atmosphere. However, as described in Japanese Unexamined Patent Publication (Kokai) No. 5-92141, the problem occurs in that Cr scatters at the time of fluorination of the precursor which is carried out after firing. Accordingly, when the support described above is used, too, firing is conducted in the inert gas or reducing gas atmosphere. Alternatively, after firing is once carried out in the inert gas, it is preferably carried out further in the reducing gas atmosphere.

A further preferred method is the one which disposes a step of heat-treatment in the reducing gas atmosphere in the sintering process. In other words, when the chromium compound is used as the principal component of the catalyst precursor or when active carbon is used as the support, firing is directly made in the reducing gas atmosphere after the drying step. Alternatively, after firing is once made in the inert gas, it is further carried out preferably in the reducing gas atmosphere. When alumina and various metal fluorides are used as the support, firing is carried out directly in the reducing gas atmosphere after the drying step, or after firing is once made in the $O_2$-containing atmosphere, it is preferably carried out further in the reducing gas atmosphere.

When heat-treatment is conducted in the reducing gas atmosphere as described above, the quantity of scattering Cr at the time of fluorination of the catalyst precursor before the reaction can be reduced, and the catalytic activity can be improved. Further, other effects can also be expected. The heat-treating temperature is suitably within the range of 350° to 500° C., preferably from 370° to 460° C., and most preferably from 370° to 450° C. The kind of the reducing gas used is $H_2$, CO, NO, and so forth, but $H_2$ can be appropriately used because it is easy to handle. The concentration of the reducing gas is from 0.1 to 100 vol %, and not greater than 20 vol % of water or not greater than 99.9 vol % of an inert gas may be co-present in the gas, whenever necessary. However, the $O_2$ concentration must be restricted to below 0.1 vol % from the aspect of safety. The gas flow rate is suitably from 10 to 1,000 $h^{-1}$ in terms of GHSV (converted to the standard state), and a pressure ranging from the atmospheric pressure to 10 kg/cm$^2$ is easy to handle. The heat-treating time is at least 30 minutes and preferably, from 1 to 10 hours.

It is not preferred to expose the catalyst precursor heat-treated in the reducing gas atmosphere to an atmosphere having a pressure of $O_2$ of at least 1,000 Pa in terms of the absolute pressure at a high temperature. Accordingly, after the precursor is fired in the reducing gas atmosphere, it should not be fired further in the atmosphere containing $O_2$ such as in the air. Further, when the atmosphere in the system is replaced with air at the time of withdrawal of the precursor after completion of firing in the reducing gas atmosphere, an operation which introduces $O_2$ into the reaction system at a temperature of higher than 200° C. should be avoided. In other words, the pressure should be released to the atmospheric pressure by introducing little by little air into the system preferably at 150° C. and further preferably, below 120° C., so as to gradually increase the $O_2$ concentration inside the system.

Preparation of the catalyst precursor may be conducted by any of the methods described above or by any of the heretofore known methods, but the atomic ratio of Ga to Cr (hereinafter called "Ga/Cr ratio") must be kept within the range of 0.0001 to 0.15, preferably 0.001 to 0.1 and particularly preferably 0.003 to 0.05. If the Ga/Cr ratio is smaller than the range described above, the effect of preventing coking cannot be obtained and if the Ga/Cr ratio is too great, the reaction rate drops undesirably. The Ga/Cr ratio can be easily controlled by regulating the proportion of powders to be mixed in the case of the kneading method and by controlling the concentrations of the Ga and/or Cr compound solutions and the composition of the solutions in the case of the impregnation method and the coprecipitation method.

The fluorination catalyst according to the present invention further requires O and F as the essential constituent elements. Though the suitable ranges of the O and F contents change in accordance with the Ga/Cr ratio and with the preparation method of the catalyst precursor, at least 0.3 wt %, on the basis of the total weight of the catalyst, is necessary for each of the components. A preferred range of the 0 content is from 1 to 25 wt %, and a preferred F content is from 15 to 45 wt %. In order to allow the catalyst to contain O and F, the compound containing Ga and Cr is fluorinated by a gas of HF, $F_2$ or a halogenated hydrocarbon containing F in the molecule thereof, as already described. Among them, the fluorination method using HF is excellent from the aspect of the cost.

The fluorination temperature of the catalyst precursor before the reaction is from 300° to 500° C. and particularly preferably, from 300° to 450° C. The concentration of the fluorinating agent such as HF may be from 0.1 to 100 vol %, but the fluorinating agent is preferably diluted by an inert gas such as $N_2$, whenever necessary, so that the temperature rise (hereinafter called "$\Delta T$") due to exothermy is at most 50° C. A suitable gas flow rate is 10 to 10,000 $h^{-1}$ by GHSV, and the pressure ranges from the atmospheric pressure to 20 kg/cm$^2$G.

A preferred example of the fluorination method of the catalyst precursor supplies HF and $N_2$ at the atmospheric pressure and at 300° to 400° C. so that the HF concentration becomes 5 to 30 vol %, and then starts fluorination. After a hot spot passes through the precursor packing layer, the HF concentration and the pressure are raised to at least 90 vol % and 2 to 10 kg/cm$^2$G, respectively, while caution is paid to exothermy, and treatment is continued under the final condition until at least exothermy no longer exists.

Firing of the catalyst precursor and its fluorination described above can be carried out inside the same reactor so long as it is made of Inconel or Hastelloy, and the operation can be conveniently made.

The fluorination catalyst which contains Ga, Cr, O and F as the essential constituent elements and can be produced in the manner described above can be applied to fluorination of halogenated hydrocarbons by HF, and is particularly effective for the fluorination reaction of H-containing halogenated hydrocarbons. In other words, coking more difficultly proceeds than in the conventional fluorination catalysts such as chromium oxyfluoride, and longer catalyst life can be accomplished.

The term "H-containing halogenated hydrocarbons" used in the present invention represents those halogenated hydrocarbons which contain H mainly in C1 to C4 molecules, and concrete examples include $CHCl_3$, $CH_2Cl_2$, $CH_2FCl$, $CH_3Cl$, $C_2HCl_3$, $C_2H_2Cl_2$, $C_2H_3Cl$, $C_2HCl_5$, $C_2HFCl_4$, $C_2HF_2Cl_3$, $C_2HF_3Cl_2$, $C_2HF_4Cl$ , $C_2H_2Cl_4$, $C_2H_2FCl_3$, $C_2H_2F_2Cl_2$, $C_2H_2F_3Cl$, $C_2H_3Cl_3$, $C_2H_3FCl_2$, $C_2H_3F_2Cl$, $C_2H_4Cl_2$, $C_2H_4FCl$, $C_2H_5Cl$, $C_3H_2F_4Cl_2$, and $C_3HF_4Cl_3$. Further, Cl of the hydrocarbons described above may be replaced either completely or partially by Br. Among others, the fluorination catalyst of the present invention is effective for the fluorination reaction of $CH_2Cl_2$, $CH_2FCl$ (HCFC-31), $CHCl=CCl_2$ (trichloroethylene), $CF_2CH_2Cl$ (HCFC-133a), $CCl_2=CCl_2$ (perchloroethylene), $CF_3CHCl_2$ (HCFC-123), $CF_3CHFCl$ (HCFC-124), etc., which are believed as a synthesis route for the production of $CH_2F_2$ (HFC-32), $CH_2FCF_3$ (HFC-134a) and $CF_3CHF_2$ (HFC-125) which have drawn an increasing attention in recent years as the HFCs which are free from possible destruction of the ozone layer.

The fluorination reaction may take the reaction method such as a fixed bed, a fluidized bed, a moving bed, etc., but generally, the molar ratio of HF to the halogenated hydrocarbon is 0.5 to 20, the temperature is from 200° to 400° C., the pressure is from the atmospheric pressure to 20 kg/cm$^2$G, and SV is from 50° to 100,000 $h^{-1}$. Since coking does not easily proceed in the fluorination catalyst of the present invention, the molar ratio of HF to the halogenated hydrocarbons can be made smaller than in the case where the conventional fluorination catalysts are used. Accordingly, not only catalyst life can be improved, but high STY can also be improved and hence, productivity can be improved.

EXAMPLES

Hereinafter, the present invention will be concretely explained with reference to Examples and Comparative Examples, but the invention is not limited to such an explanation. The Ga/Cr ratio represents the atomic ratio of each element contained in the catalyst determined by chemical analysis, and the molar ratio in the reaction example represents the molar ratio of HF to the halogenated hydrocarbons. SV is a value converted to the standard condition, and the pressure is a gauge pressure.

Catalyst Preparation Example 1

A Ga and Cr-containing aqueous solution was obtained by dissolving 0.92 g of $Ga(NO_3)_3$. $nH_2O$ (Ga content: 18.9 wt %) and 10 g of $Cr(NO_3)_3 \cdot 9H_2O$ in 240 g of pure water.

Next, aqueous ammonia ($NH_3$) was further added to a slurry of chromium hydroxide prepared by mixing an aqueous $Cr(NO_3)_3$ solution with aqueous ammonia. After pH of the slurry (Cr content in the slurry=1.4 wt %) was adjusted to 9 in this way, the Ga and Cr-containing aqueous solution described above was added dropwise to 840 g of this slurry in the course of about 20 minutes so as to prepare the slurry of hydroxide containing Ga and Cr. The resulting slurry was filtrated, was sufficiently washed with pure water and was dried at 110° C. for 12 hours. The resulting solid was pulverized, was mixed with graphite and was thereafter pelletized by a tableting machine.

The pellet was packed into a firing tube and was fired at 400° C. for 4 hours in the $H_2$ stream to obtain a catalyst precursor. The resulting precursor was packed into a reaction tube made of Inconel and was subjected to the fluorination treatment first in a 20 vol % HF stream diluted by $N_2$ at 350° C. and the atmospheric pressure, then in a 100 vol % HF stream while the supply of $N_2$ was cut off, and further in a 100 vol % HF stream while the pressure was raised to 5 $kg/cm^2 G$. The composition of the pellet after this treatment is tabulated below:

Ga: 0.79, Cr: 58.6, O: 19.1, F: 19.5

The result of analysis represents that the Ga/Cr ratio was 0.01.

Catalyst Preparation Example 2

A slurry of chromium hydroxide prepared by mixing an aqueous $Cr(NO_3)_3$ solution and aqueous ammonia ($NH_3$) with sufficient stirring was filtered, and the filtrate was sufficiently washed by pure water and was then dried at 110° C. for 12 hours. The resulting solid was pulverized, and an aqueous GaCl solution (prepared by dissolving 0.43 g of GaCl in 25 g of pure water) was slowly dropped to 50 g of the pulverizate so obtained. The powder thus wetted was again dried at 110° C. for 12 hours, was then mixed with graphite and was thereafter pelletized by a pelletizing machine. Thereafter, the fluorination treatment was carried out in the same way as in Preparation Example 1. The composition of the pellet after this treatment is tabulated below.

Ga: 0.39, Cr: 57.5, O: 18.0, F: 21.0

The result of analysis represents that the Ga/Cr ratio was 0.005.

Comparative Catalyst Preparation Example 1

A catalyst precursor not containing Ga was prepared by following the procedures of Preparation Example 1 except that $Ga(NO_3)_3 \cdot nH_2O$ was not added to the aqueous solution to be added dropwise to the slurry of chromium hydroxide. The resulting catalyst precursor was subjected to the fluorination treatment in the same way as in Preparation Example 1. The composition of the pellet after this treatment is tabulated below.

Cr: 58.9, O: 18.5, F: 20.6

Comparative Catalyst Preparation Example 2

A catalyst precursor having a large addition amount of Ga was prepared by following the procedures of Preparation Example 1 except that 18.4 g of $Ga(NO_3)_3 \cdot nH_2O$ was added to the aqueous solution to be added dropwise to the slurry of chromium hydroxide, and the resulting catalyst precursor was subjected to the fluorination treatment in the same way as in Preparation Example 1. The composition of the pellet after this treatment is tabulated below.

Ga: 12.4, Cr: 46.5, O: 16.7, F: 21.4

The result of analysis represents that the Ga/Cr ratio was 0.2.

Catalyst Preparation Example 3

A catalyst was prepared in the same way as in Preparation Example 1 except that the pellet molded in Preparation Example 1 was fired at 400° C. in the $N_2$ stream. The Ga/Cr ratio determined by the result of analysis was 0.01.

Catalyst Preparation Example 4

A solution prepared by dissolving 75 g of $Cr(NO_3)_3 \cdot 9H_2O$ and 0.69 g of $Ga(NO_3)_3 \cdot nH_2O$ in 200 me of pure water and 50 ml of 28 wt % aqueous ammonia were charged dropwise into a 1 l container storing therein 100 ml of pure water in the course of about 20 minutes while the flow rates of two kinds of aqueous solutions were controlled so that the pH of the reaction solution was within the range of 7.5 to 8.5. The resulting slurry was filtrated, was sufficiently washed by pure water and was thereafter dried at 110° C. for 12 hours. The catalyst was prepared by thereafter following the procedures of Preparation Example 1. The Ga/Cr ratio determined from the result of analysis was 0.01.

Catalyst Preparation Example 5

After 110 g of $CrCl_3 \cdot 6H_2O$ and 0.58 g of $GaCl_3$ were dissolved in 78 g of pure water, 100 g of activated alumina was immersed in the solution so as to absorb the full amount of the solution. The alumina was then dried at 120° C. for 12 hours and was packed into a firing tube made of glass. Firing was carried out first at 350° C. for 3 hours in air stream and then at 400° C. for 4 hours in the $H_2$ stream. The resulting precursor was packed into a reaction tube made of Inconel, and the fluorination treatment was carried out first at 350° C. and the atmospheric pressure in a 20 vol % HF stream treated by $N_2$, then in a 100 vol % HF stream while the feed of $N_2$ was cut off, and further in a 100 vol % HF stream while the pressure was raised to 3 $kg/cm^2 G$.

The Ga/Cr ratio determined from the result of analysis of 0.008.

Catalyst Preparation Example 6

The catalyst was prepared by following the procedures of Preparation Example 1 except that an aqueous solution containing Ga, Cr and Zn prepared by additionally adding 2.97 g of $Zn(NO_3)_2 \cdot 6H_2O$ to the Ga- and Cr-containing aqueous solution used in Preparation Example 1.

The Ga/Cr ratio determined from the result of analysis was 0.01, and the Zn/Cr ratio was 0.04.

Reaction Example 1

The catalyst prepared in Catalyst Preparation Example 1 was pulverized and classified, and 2.5 ml of granules between 0.71 ml and 1 mm were packed into a reaction tube made of Inconel. Then, the fluorination reaction of HCFC-133a was carried out under the following activity evaluation condition and HFC-134a yield was measured. Thereafter, the reaction condition was changed to the following condition in which degradation was likely to occur (hereinafter called the "accelerated degradation condition"), and the reaction product was left standing for 15 hours. However, the HFC-134a yield remained at a constant value of about 11%. Thereafter, the reaction condition was again returned to the activity evaluation condition described above, and the degree of the drop of activity was measured. Table 1 illustrates the HFC-134a yields before and after accelerated degradation and a yield ratio before and after accelerated degradation.

Activity evaluation condition:
temperature: 320° C.,
pressure: atmospheric pressure,
HF/HCFC-133a molar ratio: 8,
SV: 1,500 h$^{-1}$
Accelerated degradation condition:
temperature: 360° C.,
pressure: atmospheric pressure,
HF/HCFC-133a molar ratio: 1,
SV: 2,000 h$^{-1}$ Reaction Example 2

The degree of drop of activity due to accelerated degradation was measured in accordance with Reaction Example 1 except that the catalyst prepared in Catalyst Preparation Example 2 was used. The result is tabulated in Table 1.

Comparative Reaction Example 1

The degree of the drop of activity due to accelerated degradation was measured in accordance with Reaction Example 1 except that the catalyst prepared in Comparative Catalyst Preparation Example 1 was used. The result is tabulated in Table 1.

Comparative Reaction Example 2

The degree of the drop of activity due to accelerated degradation was measured in accordance with Reaction Example 1 except that the catalyst prepared in Comparative Catalyst Preparation Example 1 was used. The result was tabulated in Table 1.

TABLE 1

Yield comparison of HFC-134a before and after accelerated degradation

| catalyst | yield before acc-deg.* (%) | yield after acc-deg.* (%) | yield ratio |
|---|---|---|---|
| Prep. Example 1 | 24.1 | 16.9 | 0.70 |
| Prep. Example 2 | 21.0 | 16.2 | 0.77 |
| Comp. Prep. Ex. 1 | 23.8 | 10.3 | 0.43 |
| Comp. Prep. Ex. 2 | 12.4 | 9.2 | 0.74 |

*accelerated degradation

In the table above, the yield represents the yield of HFC-134a and the yield ratio represents the ratio of the yields before and after accelerated degradation.

It could be understood from the result described above that in the case of the catalyst containing Ga added thereto, coking was difficult to occur even when the catalyst was exposed to the reaction condition where degradation was likely to occur, and consequently, the degree of the drop of activity was small. It could also be understood from Comparison Reaction Example 2 that if the amount of addition of Ga was too great, activity of the catalyst undesirably dropped.

Reaction Examples 3 to 6

The degree of the drop of activity due to accelerated degradation was measured in the same way as in Reaction Example 1 except that the catalysts prepared in Catalyst Preparation Examples 3 et seq were used. Table 2 illustrates the HFC-134a yield ratios before and after accelerated degradation.

TABLE 2

HFC-134a yield ratios before and after accelerated degradation

| catalyst | yield ratio |
|---|---|
| Preparation Example 3 | 0.71 |
| Preparation Example 4 | 0.77 |
| Preparation Example 5 | 0.63 |
| Preparation Example 6 | 0.70 |

In the table, the yield represents the yield of HFC-134a, and the yield ratio represents the ratio of the yields before and after accelerated degradation.

Reaction Example 7

The fluorination reaction of HCFC-123 was carried out under the following condition using the catalyst prepared in Catalyst Preparation Example 1 in accordance with Reaction Example 1, and the degree of the drop of activity was measured.

Activity evaluation condition:
temperature: 320° C.,
pressure: atmospheric pressure,
HF/HCFC-133a molar ratio: 4,
SV: 1,000 h$^{-1}$
Accelerated degradation condition:
temperature: 370° C.,
pressure: atmospheric pressure,
HF/HCFC-133a molar ratio: 1,
SV: 1,000 h$^{-1}$ The yield ratio of HFC-125 before and after accelerated degradation was 0.48.

As described above, since the fluorination catalyst according to the present invention has long service life, it can produce hydrofluorocarbons with high productivity.

We claim:
1. A chromium-based fluorination catalyst containing chromium, gallium, oxygen and fluorine as essential constituent elements, wherein an atomic ratio of gallium to chromium is within a range of 0.001 to 0.15.
2. A chromium-based fluorination catalyst according to claim 1, wherein the atomic ratio of gallium to chromium is within a range of 0.003 to 0.05.
3. A chromium-based fluorination catalyst according to claim 1, which further contains at least one element selected from the group consisting of cobalt, nickel, zinc and cadmium in an atomic ratio amount of from 0.001 to 0.5 with respect to chromium.
4. A method for producing a chromium-based fluorination catalyst according to claim 1, comprising bringing a catalyst precursor containing chromium and gallium into contact with an F$_2$ gas, hydrogen fluoride or a fluorine-containing hydrocarbon, and carrying out fluorination treatment to obtain said catalyst.

5. A method according to claim 4, wherein said catalyst precursor is an oxide and/or a hydroxide.

6. A method according to claim 5, wherein said catalyst precursor is prepared by a coprecipitation method.

7. A method according to claim 5, wherein said catalyst precursor is prepared by an impregnation method.

8. A method according to claim 4, which uses a catalyst precursor heat-treated at a temperature of from 350° to 500° C. in an atmosphere containing a reducing gas.

9. A method according to claim 8, wherein said reducing gas is hydrogen.

* * * * *